(12) United States Patent
Ostermeier

(10) Patent No.: US 7,404,672 B2
(45) Date of Patent: Jul. 29, 2008

(54) METHOD FOR SUPPORTING A MINIMALLY INVASIVE INTERVENTION ON AN ORGAN

(75) Inventor: Martin Ostermeier, Buckenhof (DE)

(73) Assignee: Siemens Aktiengesellschaft, Munich (DE)

(*) Notice: Subject to any disclaimer, the term of this patent is extended or adjusted under 35 U.S.C. 154(b) by 195 days.

(21) Appl. No.: 11/387,524

(22) Filed: Mar. 23, 2006

(65) Prior Publication Data

US 2006/0215812 A1 Sep. 28, 2006

(30) Foreign Application Priority Data

Mar. 24, 2005 (DE) .................. 10 2005 013 835

(51) Int. Cl.
*A61B 6/08* (2006.01)
*G01N 23/04* (2006.01)

(52) U.S. Cl. ..................... 378/205; 378/62; 378/65
(58) Field of Classification Search ............. 378/62, 378/65, 205
See application file for complete search history.

(56) References Cited

U.S. PATENT DOCUMENTS

| | | | | |
|---|---|---|---|---|
| 6,064,904 A | * | 5/2000 | Yanof et al. | 600/414 |
| 6,487,431 B1 | * | 11/2002 | Iwano et al. | 600/407 |
| 6,690,964 B2 | * | 2/2004 | Bieger et al. | 600/424 |
| 2002/0058868 A1 | | 5/2002 | Hoshino et al. | |

FOREIGN PATENT DOCUMENTS

| | | |
|---|---|---|
| DE | 36 23 082 C2 | 8/1994 |
| DE | 44 17 414 A1 | 12/1994 |

* cited by examiner

*Primary Examiner*—Edward J. Glick
*Assistant Examiner*—Thomas R Artman

(57) ABSTRACT

A method for supporting a minimally invasive intervention on an organ makes use of the fact that modern X-ray angiography systems provide three-dimensional information about organs, on the basis of which start and target points can be indicated for the intervention. A connecting line can be calculated between the start and target points and subsequently recorded two-dimensional X-ray images can show this connecting line.

4 Claims, 1 Drawing Sheet

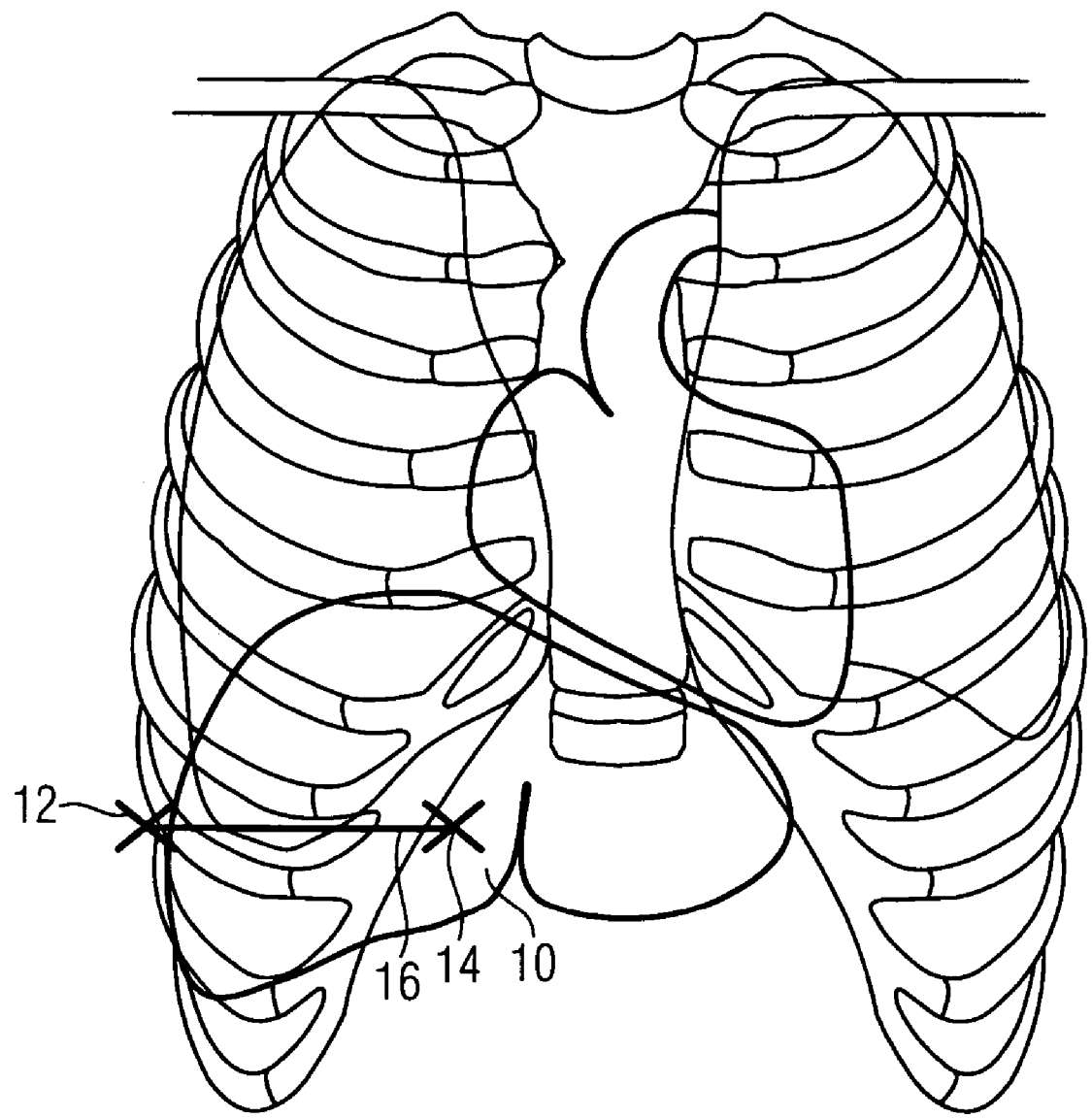

METHOD FOR SUPPORTING A MINIMALLY INVASIVE INTERVENTION ON AN ORGAN

CROSS REFERENCE TO RELATED APPLICATIONS

This application claims priority to the German Application No. 10 2005 013 835.7, filed Mar. 24, 2005 which is incorporated by reference herein in its en tirety.

FIELD OF INVENTION

The invention relates to a method for supporting a minimally invasive intervention, for example a puncture, on an organ.

BACKGROUND OF INVENTION

When carrying out a minimally invasive intervention, such as an organ puncture, for example a liver puncture through the abdominal wall of the patient, to reach the puncture target such as the bile duct in the liver, until now two-dimensional image information has been supplied by means of an X-ray angiography system. During the puncture the radiologist can find their way in the three-dimensional space using successive fluoroscopy images with different angulations of the C-arm of the X-ray angiography system. A plurality of images must therefore be recorded before the puncture target is reached. The time and exposure required to do this is significant and also greatly dependent on the experience of the user.

A stereo X-ray device is known from DE 36 23 082 C2, with which a signal is generated, which is superimposed on the stereo image generated by the device as a target marker for an organ puncture.

SUMMARY OF INVENTION

It is known from U.S. 2002/0058868 A1 that preparations can be made for a puncture using images obtained using nuclear magnetic resonance. As part of these preparations a target point and a start point for a puncture needle are input in a 3-D image set. A connecting line is determined by computation between the start point and the target point. During the puncture the position of the puncture needle is captured. Deviations from the connecting line, in particular also of the needle angle, are determined by computation. An alarm signal is emitted by the system based on the deviations.

An image processing method for medical support for stereotactic operations is known from DE 44 17 414 A1. Two orthogonal projections are used here. A target point and a penetration point are selected to determine the trajectory of a needle. A cylindrical surface is marked on both images, to show the path of the needle.

There is no further technical support for a minimally invasive intervention such as a puncture in the prior art.

It is desirable for supporting data to be available during a puncture, to minimize the time and X-ray exposure involved.

This object is achieved by the claims.

The method for supporting a puncture on an organ makes use of the fact that it has recently become possible to carry out imaging in a similar manner to computed tomography with the C-arm of an X-ray angiography system, in other words to generate a large number of sectional images based on an image sequence. The sectional images have a soft tissue resolution, which is adequate to identify a puncture target in a target organ, e.g. the bile duct filled with bile. The claimed method has the following steps:

a) Deployment of rotational angiography and capturing of the image data for a plurality of X-ray images of an anatomical region of interest using an X-ray angiography system,
b) Displaying of the image data for a three-dimensional view,
c) Inputting of a start point for the intervention and a target point for the intervention and transfer of the data for the start and target points to the X-ray angiography system,
d) Calculating a connecting line between the start and target points and
e) Recording any two-dimensional X-ray images of the organ and marking the connecting line in displays of the X-ray images.

The claimed method therefore uses the three-dimensional view that is now possible in X-ray angiography, generally resulting from mapping three mutually orthogonal sectional planes through the organ. These sectional images can be used to define the start and target points for the intervention, for example a puncture, and the coordinates of these points can be transferred to the X-ray angiography system, in particular its image processing unit, by simply inputting them with a mouse. The angiography system can use this information to display the optimum path for guiding the needle in the fluoroscopy image. In step e), after inputting the start and target points for the puncture, a connecting line between these two points can be displayed in the X-ray image in any perspective. The doctor carrying out the puncture will record the two-dimensional X-ray images such that they provide the best possible assistance when guiding the needle. Any C-arm angulation can be selected to this end.

In a preferred embodiment, after step d) one or more optimum imaging situations are determined. For example a two-dimensional image can be selected, in which the connecting line between the start and target points extends across the image and preferably at the same depth in the image. In other words the C-arm angulation can be selected such that the two dimensions of the X-ray image form a plane parallel to a plane in which the puncture needle is to be guided, in other words in which the connecting line is located.

According to a preferred embodiment, these determined optimum imaging situations are indicated before step e), in other words displayed on a screen or the associated information relating to the recording parameters is output in another appropriate manner, for example as parameterization of an automatic movement of the C-arm into the corresponding angulation, such that the radiologist or doctor carrying out the treatment can use them to record two-dimensional X-ray images.

The invention can be used for punctures from outside as well as for minimally invasive drainage processes or biopsies within the body after intravasal access, e.g. for TIPS, Transjugular Intrahepatic Portosystemic Stent, procedures, because the TIPS procedure also leaves the vascular system and a puncture is carried out outside the vascular system.

BRIEF DESCRIPTION OF THE DRAWING

The invention is described below with reference to the drawing, in which:

FIG. 1 shows a schematic diagram of parts of the body of a patient, as they could be imaged in the X-ray image, and an exemplary line therein for guiding a puncture needle.

DETAILED DESCRIPTION OF INVENTION

The method for supporting a minimally invasive intervention starts with rotational angiography. During rotational angiography 250 to 500 X-ray images are recorded for angles over a range of around 200° at the C-arm of an X-ray angiography system. So-called voxel information is obtained from these X-ray images, i.e. information relating to volume elements of the patient's body. After recording the 250 to 500 images, each of the volume elements is captured as part of the image resolution process and a three-dimensional view is possible. The X-ray angiography system or its associated image processing system uses the many recorded X-ray images to calculate sectional images through the patient or through the captured organ and maps three mutually orthogonal sectional images on the screen.

The radiologist can "leaf through" these sectional images layer by layer, in other words it is possible to look through the sectional images for one layer after another. The depth of the respective layer can be indicated by a simple line in the two orthogonal sectional images.

The soft-tissue resolution of the sectional images is of adequate quality with current X-ray angiography systems to be able to identify a target organ, such as a bile duct, so precisely that the target of the minimally invasive intervention, for example a puncture, can be defined. The radiologist can now use a mouse to mark a point so to speak with a cross, in other words mark it by a mouse click, in a suitable sectional image, the image processing system of the X-ray angiography system being configured such that the coordinates predefined by the mouse are input or transferred to this image processing system by a mouse click. The radiologist can simply define the target point thus or can make corrections to the input target point. After being input and transferred to the image processing system, the target point is shown in both orthogonal sectional images, which supplement the sectional image, in which the selection was made. The target point can also simply be selected and moved with the mouse, such that further correction of the target point is possible, in particular in a direction that is orthogonal in respect of the original image.

The target point can also be corrected by selecting it with the mouse both in the plane, in which it was generated, and in image planes orthogonal thereto, i.e. the sectional image in which the target point was selected can also be corrected.

Finally the user (radiologist) can use the mouse or a key input to inform the image processing system that this is the final target point input.

The start point of the intervention can now be defined in the same manner as the target point of the intervention. For example a point can be selected on the abdominal wall, where the doctor carrying out the treatment is to make the first insertion for the puncture.

The start point can also be selected using the display of image data in the three-dimensional view by means of mutually orthogonal sectional images.

Once the start and target points have been selected for the intervention, a connecting line can be calculated between the start and target points. Three-dimensional coordinate points of the connecting line are hereby calculated, defined in relation to the 250 to 500 X-ray images recorded beforehand during X-ray angiography or the image processing system displaying them. It is important that the patient has not moved in the meantime.

If an additional single X-ray image is now generated two-dimensionally, the image system of the X-ray angiography system knows where the connecting line is located between the start and target points for the intervention. This connecting line can be mapped on the two-dimensional image almost from the start, as shown schematically in FIG. 1. FIG. 1 shows parts of the body of a patient, which can be mapped in the X-ray image, in particular a liver 10. Marked on the image are the start point 12 for a possible liver puncture and the target point 14 for the puncture. The connecting line 16, which can be mapped on the corresponding X-ray image, is shown between the start point 12 and the target point 14. (It should be noted that the start and target points have been selected here for reasons of clarity and no medical statement is intended).

It is clear that the connecting line can be seen particularly clearly in certain perspectives. The radiologist is required to select these perspectives, as they become clear. The image processing system of the X-ray angulation system can be of assistance here when selecting angulation angles for the C-arm of the X-ray angiography system, such that the line 16 is for example shown extended in a particular manner or is produced based on empirical values such that it is most useful to the doctor carrying out the puncture.

As with the prior art the doctor only records two-dimensional X-ray images during the actual puncture. The displayed connecting line between the start and target points of the puncture helps the doctor in a particularly fast and simple manner to find the right direction for guiding the puncture needle. This significantly reduces the time required for the intervention and also considerably reduces the total number of two-dimensional X-ray images that have to be recorded during the intervention. The doctor is able to guide the needle optimally with just a few fluoroscopy images from different angulations. The displayed connecting line, which serves as the needle guide line, is shown based on the respective angulation, such that the puncture target can be reached quickly and reliably.

The method in particular helps less experienced doctors during interventions such as punctures.

The invention claimed is:

1. A method of supporting a puncture on an organ, comprising:
   executing a rotational angiography including acquiring image data of a plurality of X-ray images displaying an anatomical region of interest using an X-ray angiography system;
   displaying the image data in a three-dimensional view;
   inputting data related to a start and a target point for the puncture;
   transferring the data related to the start and target points to the X-ray angiography system;
   calculating a connecting path between the start and target points;
   recording a plurality of two-dimensional X-ray images of the organ; and
   displaying the calculated connecting path in the plurality of X-ray images,
   wherein a three-dimensional view is created based on mapping three mutually orthogonal section planes through the organ.

2. The method according to claim 1, wherein a computer mouse is used for inputting the data related to the start and target point.

3. The method according to claim 1, further comprising determining at least one optimized imaging position before recording the plurality of two-dimensional X-ray images, wherein the plurality of two-dimensional X-ray images is recorded relative to the determined imaging position.

4. The method according to claim 1, further comprising automatically moving a C-arm of the X-ray angiography system to an optimized angular position before recording the plurality of two-dimensional X-ray images for optimizing an image quality of the plurality of X-ray images.

* * * * *